United States Patent [19]

Kollmeyer

[11] 4,025,529

[45] May 24, 1977

[54] PREPARATION OF NITROKETENE AMINALS

[75] Inventor: Willy D. Kollmeyer, Modesto, Calif.

[73] Assignee: Shell Oil Company, Houston, Tex.

[22] Filed: Sept. 8, 1975

[21] Appl. No.: 611,363

[52] U.S. Cl. .................. 260/309.6; 260/251 R; 260/465.5 R; 260/564 R; 260/564 E; 260/583 F

[51] Int. Cl.² ..................................... C07D 233/20

[58] Field of Search ........ 260/564 R, 583 F, 309.7, 260/251 R, 465.5 R

[56] References Cited

UNITED STATES PATENTS 3,948,934   4/1976   Tieman et al. ............... 260/309.6

FOREIGN PATENTS OR APPLICATIONS 48-11097   1973   Japan

OTHER PUBLICATIONS

Rajappa et al., "Synthesis", International Journal of Methods in Synthetic Organic Chemistry, 1974 (No. 9, Sept.), pp. 656 & 657.

Hirai et al., Chem. Pharm. Bull., 1972, vol. 20, pp. 97–100.

*Primary Examiner*—Natalie Trousof

[57] ABSTRACT

Nitroketene aminals are prepared by treating isothioureas with nitromethane.

3 Claims, No Drawings

PREPARATION OF NITROKETENE AMINALS

DESCRIPTION OF THE INVENTION

It has been found that nitroketene aminals of the formula

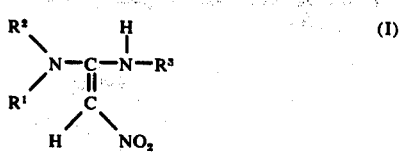

wherein the symbols have the respective meanings set out hereinafter, can be prepared by treating an isothiourea,

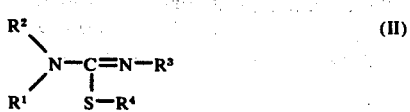

with nitromethane.

In these compounds, the symbols have the following meanings:

$R^1$, $R^2$ and $R^3$ each is alkyl, mono- or polyhaloalkyl, alkenyl, mono- or polyhalo-alkenyl, alkoxyalkyl, alkylthioalkyl, cyanoalkyl or alkynyl; with the proviso that $R^2$ and $R^3$ together can represent —CH$_2$—CH$_2$— or —CH$_2$—CH$_2$—CH$_2$—, and $R^4$ is alkyl of 1 to 4 carbon atoms, preferably methyl, or is benzyl.

In all cases, unless otherwise expressly indicated, each alkyl, alkenyl, alkynyl or alkylene moiety suitably contains up to six carbon atomms, and may be of straight-chain or branched-chain configuration.

Many of the products of the process of this invention are pesticidally, particularly insecticidally, active and/or can be used to prepare pesticidally active compounds. For example, the products of the working examples set out hereinafter are insecticidally active, as are the products which are included in U.S. patent application Ser. No. 510,100 filed Sept. 27, 1974, U.S. Pat. No. 3,948,934, issued Apr. 6, 1976. These products are those wherein $R^1$ is straight-chain alkyl, haloalkyl, alkenyl, cyanoalkyl, haloalkenyl or alkynyl, $R^2$ and $R^3$ together are —CH$_2$—CH$_2$— or —CH$_2$—CH$_2$—CH$_2$—.

The reaction between the isothiourea and nitromethane can be effected by mixing the two materials and heating the stirred mixture at a temperature of about 90° C or somewhat higher for a sufficient time to complete the reaction. Since the boiling point of nitromethane at atmospheric pressure is about 101° C, it will be found that a convenient technique often will be to employ an excess of nitromethane over that required for reaction with the isothiourea, and conducting the reaction at the reflux temperature of the reaction mixture. The excess nitromethane also acts to increase the rate of the reaction and to drive it to completion. The excess of nitromethane need not be large: sufficient to provide a mobile reaction mixture will be sufficient. In general, therefore, an excess of from 50% to about 200% on a molar basis, will generally be suitable.

A mercaptan, $R^4$-SH, is produced as a by-product. It generally will be found to be a preferable technique to effect removal of this mercaptan from the reaction mixture as it forms.

A word of warning: at least some of the isothioureas are strong bases. Since it is well known that nitromethane can react with strong bases to form hazardous, in some cases explosive, materials, the treatment of this isothiourea with nitromethane must be conducted with this fact in mind, and with due caution and appropriate, adequate safeguards.

Further, it is desirable that water and oxygen be excluded from the reaction zone, because of their possible effects upon the reactants and/or the products.

The products of the process of this invention can be isolated from the crude reaction mixture and purified by conventional methods, which are illustrated in the working examples hereinafter. When an excess of nitromethane has been used, the excess can ordinarily be removed by evaporation, if necessary under reduced pressure, following completion of the reaction. Isopropanol is a good medium for use in purifying the products by trituration.

Corresponding precursors wherein $R^1$ is alkyl, and those wherein $R^2$ and $R^3$ together are —CH$_2$—CH$_2$ or —CH$_2$—CH$_2$—CH$_2$—, can be prepared from the corresponding thiones, described in Gilli, et al., Ric. Sci., 38, 840–1 (1968); C.A. 71, 7552f (1969). This preparation is accomplished by treating the thione with a lower dialkyl sufate in an inert solvent, such as hexane, and treating the resulting intermediate with an aqueous base such as sodium hydroxide. The manner in which this conversion is carried out is described in Example 1, hereinafter. McKay, et al., J. Org. Chem., 22, 1581–3 (1957) also disclose the hydroiodide salt of the precursor wherein $R^2$ and $R^3$ together are —CH$_2$—CH$_2$—. Other pertinent references to precursors contemplated by the invention are: J. Berger, J. prakt. Chem., 311, 549–69 (1969) and references cited therein.

Precursors contemplated in this invention wherein $R^2$ and $R^3$ each represents a separate moiety, and a method for their preparation is described in U.S. Pat. No. 2,872,484.

Conduct of the process of this invention in particular instances is shown in the following examples. In all cases, the identity of the product was confirmed by elemental analysis, and by infrared and nuclear magnetic resonance spectrum analyses. In each case, the identities of the reactants and of the products are indicated not only by their names, but by identifying the moieties present therein, the symbols being those of the general formulae (I) and (II).

EXAMPLE 1

1-methyl-2-(nitromethylene)imidazolidine ($R^1$ = —CH$_3$, $R^2$ + $R^3$ = —CH$_2$—CH$_2$—)  (1)

1-methyl-2-(methylthio)-2-imidazoline  (1A)

A stirred and refluxing suspension of 332 g (2.85 moles) of 1-methyl-imidazolidine-2-thione (Gilli, et al., Ric. Sci., 38, 840–1 (1968); C.A. 71, 7552f (1969)) in 900 ml of hexane was treated dropwise with 360 g, (2.85 moles) of dimethyl sulfate. After 2 hours, the mixture was cooled and treated with a solution of 114 g (2.85 moles) of sodium hydroxide in 320 ml of water. The hexane layer was separated and dried (MgSO$_4$). The water layer was extracted with methylene chloride, and the extract was dried (MgSO$_4$). The extracts were concentrated and the residues combined and distilled to give 1A, as a liquid, b.p.: 50°–52° (0.02 Torr.).

A mixture of 130 g (1 mole) of 1A (R = —CH$_3$, R$^2$ + R$^3$ = —CH$_2$—CH$_2$—) and 122 g (2 moles) of nitromethane was heated at about 100° for 22 hours under a static nitrogen atmosphere, evolved methyl mercaptan being scrubbed in an alkali trap. Excess nitromethane (57.4 g) was then stripped at reduced pressure. The solid residue was cooled and triturated with 100 ml of ice-cold isopropyl alcohol. Upon filtration and washing with isopropyl alcohol, 93.5 g (65% yield) of 1 was obtained, as light-tan crystals, m.p.; 141°–143°.

EXAMPLE 2 hexahydro-1-methyl-2-(nitromethylene)pyrimidine (R$^1$ = CH$_3$, R$^2$ + R$^3$ = —CH$_2$—CH$_2$—CH$_2$—)  (2)

1, 4, 5, 6-tetrahydro-1-methyl-2-(methylthio)pyridimine  (2A)

This was prepared as liquid, b.p.; 56°–62° (0.02 Torr.) from tetrahydro-1-methyl-2-(1H)-pyrimidinethione (Gilli, et al., cited in Example 1) by the procedure described in Example 1.

A mixture of 1.44 g (0.01 mole) of 2A and 1.22 g (0.02 mole) of nitromethane was kept at 100° for 5 hours, evolved methyl mercaptan being removed as it formed. Then removal of excess nitromethane at reduced pressure gave an oil which quickly solidified on cooling. Trituration with ice-cold isopropyl alcohol, followed by filtration, gave 0.65 g (41% yield) of 2, as off-white crystals, m.p.: 113°–114°.

EXAMPLE 3

N,N,N$^1$-trimethyl-2-nitro-1,1-ethenediamine (R$^1$ = CH$_3$, R$^2$ = CH$_3$, R$^3$ = —CH$_3$, R$^4$ —H)  (3)

A mixture of 5.28 g (0.04 mole) of methyl trimethylcarbamimidothioate (U.S. Pat. No. 2,872,484; C.A., 53, 11238 (1959)) and 9.6 g (0.16 mole) of nitromethane was heated on a steam-bath for 1.5 hours under a nitrogen atmosphere. Excess nitromethane then was removed under reduced pressure and the residual crystalline product was triturated with ether to give 3.5 g (60% yield) of 3, as a brown solid, m.p.: 112°–114°.

The invention claimed is:

1. A process for preparing a nitroketene aminal of the formula

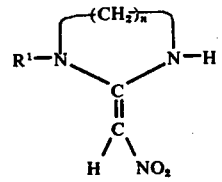

which comprises treating, in the substantial absence of water and oxygen, an isothiourea with nitromethane, said isothiourea being one defined by the formula:

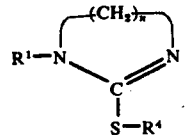

wherein R$^1$ contains up to six carbon atoms and is alkyl, mono- or polyhaloalkyl, alkenyl, mono- or polyhaloalkenyl, alkoxyalkyl, alkylthioalkyl, cyanoalkyl or alkynyl, n is 2 or 3, and R$^4$ is alkyl of 1 to 4 carbon atoms or is benzyl.

2. A process according to claim 1 wherein R$^1$ is straight-chain alkyl, haloalkyl, alkenyl, haloalkenyl or alkynyl and R$^4$ is methyl.

3. A process according to claim 2 wherein R$^1$ is methyl and n is 2.

* * * * *